US008927215B2

(12) United States Patent
Bastian et al.

(10) Patent No.: US 8,927,215 B2
(45) Date of Patent: Jan. 6, 2015

(54) GNA11 MUTATIONS IN MELANOMA

(75) Inventors: Boris C. Bastian, Mill Valley, CA (US); Catherine D. Van Raamsdonk, Vancouver (CA); Gregory S. Barsh, Huntsville, AL (US)

(73) Assignees: The Regents of the University of California, Oakland, CA (US); The University of British Columbia, Vancouver, BC (CA); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/504,928

(22) PCT Filed: Oct. 29, 2010

(86) PCT No.: PCT/US2010/054843
§ 371 (c)(1),
(2), (4) Date: Oct. 17, 2012

(87) PCT Pub. No.: WO2011/053852
PCT Pub. Date: May 5, 2011

(65) Prior Publication Data
US 2013/0058938 A1 Mar. 7, 2013

Related U.S. Application Data

(60) Provisional application No. 61/256,885, filed on Oct. 30, 2009.

(51) Int. Cl.
C12Q 1/68 (2006.01)
C12P 19/34 (2006.01)
(52) U.S. Cl.
CPC ........ *C12Q 1/6886* (2013.01); *C12Q 2600/112* (2013.01); *C12Q 2600/156* (2013.01); *C12Q 2600/106* (2013.01); *C12Q 2600/136* (2013.01)
USPC .......................................... 435/6.1; 435/91.1
(58) Field of Classification Search
CPC ........... C12Q 1/6886; C12Q 2600/112; C12Q 2600/156
See application file for complete search history.

(56) References Cited

FOREIGN PATENT DOCUMENTS

| WO | 2004/043232 A2 | 5/2004 |
| WO | 2005/047542 A1 | 5/2005 |
| WO | WO 2005/059171 A1 | 6/2005 |
| WO | 2007/048067 A2 | 4/2007 |
| WO | 2008/098208 A2 | 8/2008 |

OTHER PUBLICATIONS

Lamba et al. (PLOS one Aug. 31, 2009 vol. 4 p. e6833).*
Khalili et al; Clin. Cancer Res vol. 18, pp. 4345-4355, 2012.*
Verma et al (Nature, vol. 389, pp. 239-242, 1997).*
Juppner; Bone, vol. 17; 1995, pp. 39S-40S.*
The International Search Report from PCT/US2010/054843, dated Mar. 29, 2011.
Onken et al.; "Oncogenic mutations in GNAQ occur early in uveal melanoma"; *Investigative Ophthalmology & Visual Science*; 22 pages; manuscript published Aug. 21, 2008.
Rubio et al.; Genomic Organization of the Human Gα14 and Gαq Genes and Mutation Analysis in Chorea-Acanthocytosis (CHAC); *Genomics*; 57:84-93 (1999).
Van Raamsdonk et al; "Effects of G-protein mutations on skin color"; *Nature Genetics*; 36(9):961-968 (2004).
Ariyanayagam-Baksh et al.; "Malignant blue nevus: a case report and molecular analysis"; *Am. J. Dermatopathol.*; 25(1):21-27 (2003).
Bamford et al.; "The COSMIC (Catalogue of Somatic Mutations in Cancer) database and website"; *Br. J. Cancer*; 91: 355-358 (2004).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.* 111 :2129-2138, 1990.
International Search Report and Written Opinion from PCT/US2008/053484, dated Sep. 22, 2008 (15 pages).
Cosmic id 753546; Sample Name CP66-MEL http://www.sanger.ac.uk/perl/genetics/CGP/cosmic?action=sample;id=753546 Accessed Aug. 2, 2009 (6 pages).
Cosmic Mutation id 18200; Gene GNAQ http://www.sanger.ac.uk/perl/genetics/CGP/cosmic?action=mut$_{13}$ summary&id=18200 accessed Aug. 27, 2009 (1 page).
Curtin et al.; "Distinct Sets of Genetic Alterations in Melanoma"; *N. Engl. J. Med* .; 353(20): 2135-2147 (2005).
Fisher et al.; "Meeting report: fourth international congress of the Society for Melanoma Research"; *Pigment Cell & Melanoma Research*; 21(1): 15-26 (2008).
Kalinec et al.; "Mutated α subunit of the Gp protein induces malignant transformation in NIH 3T3 cells"; *Mol. Cell. Biol.*; 12(10): 44687-4693 (1992).
Lazar et al., "Transforming Growth Factor α: Mutation of Aspartic Acid 47 and Leucine 48 Results in Different Biological Activities," *Mol. Cell Biol.* 8:1247-1252, 1998.
Lopez et al.; "Ocular malignant melanoma and blue nevi"; *Am J Dermatopathol.*; 20(1):109-110 (1998).
Navenot et al.; "Kisspeptin-10-induced signaling of GPR54 negatively regulates chemotactic responses mediated by CXCR4: a potential mechanism for the metastasis suppressor activity of kisspeptins"; *Cancer Res.*; 65(22): 10450-10456 (2005).
Neves et al.; "G protein pathways"; *Science*; 296: 1636-1639 (2002).
Oka, Masahiro et al: "Protein kinase C in melanoma", *Cancer and Metastasis Reviews*, Kluwer Academic Publishers, Do, vol. 24, No. 2, Jun. 1, 2005, pp. 287-300.
Pollock et al.; "Melanoma mouse model implicates metabotropic glutamate signaling in melanocytic neoplasia"; *Nat. Genet.*; 34(1):108-112 (2003).
Sausville et al., "Phase I Trial of 72-Hour Continuous Infusion UCN-01 in Patients with Refractory Neoplasms," *Journal of Clinical Oncology*, 2001, 19(8): 2319-2333.

(Continued)

*Primary Examiner* — Jehanne Sitton
(74) *Attorney, Agent, or Firm* — Kilpatrick Townsend & Stockton LLP

(57) ABSTRACT

The present invention provides methods of detecting mutations in a GNA11 gene in a melanocytic neoplasm for diagnostic and prognostic purposes. The invention further provides methods of treating such melanocytic neoplasm by modulating the activity of the mutated GNA11 gene.

5 Claims, 4 Drawing Sheets

(56) References Cited

OTHER PUBLICATIONS

Singh et al.; "Lifetime prevalence of uveal melanoma in white patients with oculo(dermal) melanocytosis"; *Ophthalmology*; 105(1):195-198 (1998).

Tockman et al., "Considerations in Bringing a Cancer Biomarker to Clinical Application," *Cancer Res.*, 1992, 52:2711s-2718s.

Tschentscher et al.; "Identification of chromosomes 3, 6, and 8 aberrations in uveal melanoma by microsatellite analysis in comparison to comparative genomic hybridization"; *Cancer Genet. Cytogenet.*; 122(1):13-17 (2000).

Willmore-Payne, C., et al., "Human malignant melanoma: detection of BRAF-and c-kit-activating mutations by high-resolution amplicon melting analysis," *Human Pathology*, 2005, vol. 36(5), pp. 486-493.

Zuidervaart et al.; "Activation of the MAPK pathway is a common event in uveal melanomas although it rarely occurs through mutation of BRAF or RAS"; *Br. J. Cancer*; 92: 2032-2038 (2005).

\* cited by examiner

SEQUENCE LISTING

<160> NUMBER OF SEQ ID NOS: 8

<210> SEQ ID NO 1
<211> LENGTH: 1615
<212> TYPE: DNA
<213> ORGANISM: Homo sapiens
<220> FEATURE:
<223> OTHER INFORMATION: human guanine nucleotide binding protein
      (G-protein) GNA11 alpha subunit
<220> FEATURE:
<221> NAME/KEY: CDS
<222> LOCATION: (243)...(1322)
<223> OTHER INFORMATION: GNA11 alpha subunit

<400> SEQUENCE: 1

```
gctgcggcgg cggcgcgggc tgagtgcggc cgcgcgggag tccgcggctg gcgcggcccg     60
agcggggacc cggcggctcg ccaggcggcg gccgaggcgg ggcgggccgg cccggggccg    120
agggccggtg gccgaggccg gagggccgcg gcgggcggcg gccgaggcgg ctccggccag    180
ggccgggccg ggggccgggg ggcggcggcg ggcaggcggc cgcgtcggcc ggggccggga    240
cgatgactct ggagtccatg atggcgtgtt gcctgagcga tgaggtgaag gagtccaagc    300
ggatcaacgc cgagatcgag aagcagctgc ggcgggacaa gcgcgacgcc cggcgcgagc    360
tcaagctgct gctgctcggc acgggcgaga gcggaaagag cacgttcatc aagcagatgc    420
gcatcatcca cggcgccggc tactcggagg aggacaagcg cggcttcacc aagctcgtct    480
accagaacat cttcaccgcc atgcaggcca tgatccgggc catggagacg ctcaagatcc    540
tctacaagta cgagcagaac aaggccaatg cgctcctgat ccgggaggtg acgtggaga     600 aggtgaccac cttcgagcat cagtacgtca gtgccatcaa gaccctgtgg gaggacccgg    660
gcatccagga atgctacgac cgcaggcgcg agtaccagct ctccgactct gccaagtact    720
acctgaccga cgttgaccgc atcgccacct gggctacct gcccacccag caggacgtgc    780
tgcgggtccg cgtgcccacc accggcatca tcgagtaccc tttcgacctg agaacatca    840 tcttccggat ggtggatgtg ggggccagc ggtcggagcg gaggaagtgg atccactgct    900
ttgagaacgt gacatccatc atgtttctcg tcgccctcag cgaatacgac caagtcctgg    960
tggagtcgga caacgagaac cggatggagg agagcaaagc cctgttccgg accatcatca   1020
cctacccctg gttccagaac tcctccgtca tcctcttcct caacaagaag gacctgctgg   1080
aggacaagat cctgtactcg cacctggtgg actacttccc cgagttcgat ggtccccagc   1140
gggacgccca ggcggcgcgg gagttcatcc tgaagatgtt cgtggacctg aaccccgaca   1200
gcgacaagat catctactca cacttcacgt gtgccaccga cacggagaac atccgcttcg   1260
tgttcgcggc cgtgaaggac accatcctgc agctcaacct caaggagtac aacctggtct   1320
```

```
gagcgcccag gcccaggagg acgggatgga gacacggggc aggaccttcc ttccacggag    1380
cctgcggctg ccgggcgggt ggcgctgccg agtccgggcc ggggcctctg cccgcgggag    1440
gagatttttt tttttcatat ttttaacaaa tggttttat ttcacagtta tcagggatg     1500 tacatctctc cctccgtaca cttcgcgcac cttctcacct tttgtcaacg gcaaaggcag    1560
cctttttctg gccttgactt atggctcgct tttttctaaa aaaaaaaaaa aaaaa         1615
```

<210> SEQ ID NO 2
<211> LENGTH: 359
<212> TYPE: PRT
<213> ORGANISM: Homo sapiens
<220> FEATURE:
<223> OTHER INFORMATION: human guanine nucleotide binding protein
      (G-protein) GNA11 alpha subunit

<400> SEQUENCE: 2

```
Met Thr Leu Glu Ser Met Met Ala Cys Cys Leu Ser Asp Glu Val Lys
  1               5                  10                  15

Glu Ser Lys Arg Ile Asn Ala Glu Ile Glu Lys Gln Leu Arg Arg Asp
             20                  25                  30

Lys Arg Asp Ala Arg Arg Glu Leu Lys Leu Leu Leu Leu Gly Thr Gly
         35                  40                  45

Glu Ser Gly Lys Ser Thr Phe Ile Lys Gln Met Arg Ile Ile His Gly
     50                  55                  60

Ala Gly Tyr Ser Glu Glu Asp Lys Arg Gly Phe Thr Lys Leu Val Tyr
 65                  70                  75                  80

Gln Asn Ile Phe Thr Ala Met Gln Ala Met Ile Arg Ala Met Glu Thr
                 85                  90                  95

Leu Lys Ile Leu Tyr Lys Tyr Glu Gln Asn Lys Ala Asn Ala Leu Leu
            100                 105                 110

Ile Arg Glu Val Asp Val Glu Lys Val Thr Thr Phe Glu His Gln Tyr
        115                 120                 125

Val Ser Ala Ile Lys Thr Leu Trp Glu Asp Pro Gly Ile Gln Glu Cys
    130                 135                 140

Tyr Asp Arg Arg Arg Glu Tyr Gln Leu Ser Asp Ser Ala Lys Tyr Tyr
145                 150                 155                 160

Leu Thr Asp Val Asp Arg Ile Ala Thr Leu Gly Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Glu Asn Ile Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Asp Lys Ile Leu Tyr Ser His Leu
        275                 280                 285

Val Asp Tyr Phe Pro Glu Phe Asp Gly Pro Gln Arg Asp Ala Gln Ala
    290                 295                 300

Ala Arg Glu Phe Ile Leu Lys Met Phe Val Asp Leu Asn Pro Asp Ser
```

```
                    305                 310                 315                 320
Asp Lys Ile Ile Tyr Ser His Phe Thr Cys Ala Thr Asp Thr Glu Asn
                        325                 330                 335

Ile Arg Phe Val Phe Ala Ala Val Lys Asp Thr Ile Leu Gln Leu Asn
                    340                 345                 350

Leu Lys Glu Tyr Asn Leu Val
            355

<210> SEQ ID NO 3
<211> LENGTH: 20
<212> TYPE: DNA
<213> ORGANISM: Artificial Sequence
<220> FEATURE:
<223> OTHER INFORMATION: synthetic protein kinase C (PKC)-alpha
      antisense molecule

<400> SEQUENCE: 3
gttctcgctg gtgagtttca                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic PCR amplification primer

<400> SEQUENCE: 4
cgctgtgtcc tttcaggatg                                                    20

<210> SEQ ID NO 5
<211> LENGTH: 18
<212> TYPE: DNA
<213> ORGANISM: Artificial Sequence
<220> FEATURE:
<223> OTHER INFORMATION: synthetic PCR amplification primer

<400> SEQUENCE: 5
ccacctcgtt gtccgact                                                      18

<210> SEQ ID NO 6
<211> LENGTH: 6
<212> TYPE: PRT
<213> ORGANISM: Artificial Sequence
<220> FEATURE:
<223> OTHER INFORMATION: synthetic Galphaq residues 171-176

<400> SEQUENCE: 6

Ala Tyr Leu Pro Thr Gln
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic Galpha11 residues 171-176

<400> SEQUENCE: 7

Gly Tyr Leu Pro Thr Gln
1               5

<210> SEQ ID NO 8
<211> LENGTH: 6
<212> TYPE: PRT
<213> ORGANISM: Artificial Sequence
```

```
<220> FEATURE:
<223> OTHER INFORMATION: synthetic altered Galphaq or Galpha11 residues
      171-176

<400> SEQUENCE: 8

Glu Tyr Met Pro Thr Glu
1               5
```

GNA11 MUTATIONS IN MELANOMA

CROSS-REFERENCE TO RELATED APPLICATIONS

This application is the U.S. National Stage entry of International Application No. PCT/US2010/054843, filed Oct. 29, 2010 which claims benefit of U.S. provisional application No. 61/256,885, filed Oct. 30, 2009, each of which application is herein incorporated by reference.

STATEMENT AS TO RIGHTS TO INVENTIONS MADE UNDER FEDERALLY SPONSORED RESEARCH OR DEVELOPMENT

This invention was made with Government support under grant no. R01 CA131524-01A1 awarded by the National Institutes of Health. The Government has certain rights in this invention.

REFERENCE TO A "SEQUENCE LISTING" SUBMITTED AS AN ASCII TEXT FILE

The Sequence Listing written in file SEQTXT_81906-838386_199410.TXT, created on Apr. 27, 2012, 6,783 bytes, machine format IBM-PC, MS-Windows operating system, is hereby incorporated by reference in its entirety for all purposes.

BACKGROUND OF THE INVENTION

The current model of melanoma formation is that melanocytes progress from a normal to malignant state by accumulating mutations in key melanoma genes. See, Meier, F., et al. (1998) *Frontiers in Bioscience* 3:D1005-1010. Melanoma can arise spontaneously, or within a pre-existing nevus or mole. Nevi possess mutations in known melanoma genes and are therefore a risk factor for developing melanoma. See, e.g., Pollock, P. M., et al., (2003) *Nat. Genet.* 33(1):19-20; Kumar, R. et al., (2004) *J. Invest. Dermatol.* 122(2):342-348; Chin, L., (2003) *Nat. Rev. Cancer* 3(8):559-570.

The majority of human melanomas and melanocytic nevi have been shown to have activating mutations in the BRAF, NRAS, C-KIT, or HRAS genes. Furthermore, recent studies have demonstrated that melanomas fall into genetically distinct groups having marked differences in the frequency of MAP-kinase pathway activation. See, Curtin, J. A., et al., (2005) *N Engl J Med.* 353(20):2135-47. One category, uveal melanoma, arises from melanocytes within the choroidal plexus of the eye and is biologically distinct from cutaneous melanoma by characteristic cytogenetic alterations. See, Horsman et al. (1993) *Cancer* 71(3):811. The other category are intradermal melanocytic proliferations, which can be congenital or acquired, and present in diverse ways ranging from discrete bluish moles (blue nevi) to large blue-gray patches affecting the conjunctiva and periorbital skin (nevus of Ota), shoulders (nevus of Ito), and the lower back (Mongolain spot). See, Zembowicz, et al. (2004) *Histopathology* 45(5):433. These intradermal melanocytic proliferations do not contain either BRAF or NRAS mutations, and thus have a unique eitiology when compared with other nevi and melanoma. See, Ariyanayagam-Baksh S M, et al., (2003) *Am J Dermatopathol.* 25(1): p. 21-7.

Uveal melanoma is a melanocytic neoplasm that arises from melanocytes in the choroidal plexus, ciliary body or iris epithelium of the eye (e.g., Singh, et al., *Ophthalmol Clin North Am* 18:75-84, viii, 2005). In more aggressive subtypes there are further genetic alterations such as monosomy 3, trisomy 8 and a strong tendency to metastasize to the liver (Singh, et al., *Ophthalmol Clin North Am* 18:75-84, viii, 2005, Horsman & White, *Cancer* 71:811-9, 1993). Uveal melanoma is highly aggressive, with a 5-year disease-specific survival rate of approximately 70% (e.g., Chang et al., *Cancer* 83:1664-78, 1998). One risk factor for uveal melanoma is the presence of bluish-grey hyper-pigmentation in the conjunctiva and periorbital dermis, called the naevus of Ota (Singh et al., *Ophthalmology* 105:195-8, 1998). (1998) *Am J Dermatopathol.* 20:109-110).

Recently, a large-scale mutagenesis screen in mice identified several dark skin (Dsk) mutants. See, Van Raamsdonk C D, et al., (2004) *Nat Genet.* 36: 961-968. Some of these mutants had a melanocytic phenotype with a sparse cellular proliferation of intradermal melanocytes resembling blue nevi. The mutations were shown to be the result of mutations in G-protein α-subunits.

G proteins represent a large family of heterotrimeric proteins found in mammals composed of alpha (α), beta (β) and gamma (γ) subunits. See, Wettschureck, N. A. O. S., (2005) *Physiol. Rev.* 85(4):1159-1204. G-αq, is one of a variety of G-alpha subunits that mediates the stimulation of phospholipase Cβ through the binding and hydrolysis of GTP. See, Markby, D. W., et al., (1993) *Science* 262(1541):1895-1901. It has been hypothesized that activation of G-αq promotes the survival of melanocytes in the dermis. See, Van Raamsdonk, C. D., et al., (2004). This is consistent with the observation in mice that hyperactivity of G-αq increases the number of melanoblasts, immature melanocytes, migrating in the dermis without increasing their mitotic rate. See, Van Raamsdonk, C. D., et al., (2004).

Somatic oncogenic mutations of GNAQ, a heterotrimeric G protein alpha subunit, have been identified in various melanocytic neoplasms, including blue nevi and uveal melanomas (WO 2008/098208), among others.

GNA11 is 90% identical to GNAQ at the amino acid level and shares overlapping functions with GNAQ on pigmentation in mice. This invention is based, in part, on the discovery of the occurrence of mutations in GNA11 in melanocytic neoplasms, including in uveal melanoma.

BRIEF SUMMARY OF THE INVENTION

The current invention provides methods of detecting a melanoma or nevus cell in a biological sample. The methods comprise detecting an activating sequence mutation in a GNA11 gene in a biological sample comprising the suspected melanoma cell or nevus cell, or a biological sample comprising a cell known to be a melanoma or nevus cell, from a patient. For example, the invention provides methods of detecting melanoma, e.g., either primary or metastatic uveal melanoma; or detecting a nevus, e.g, a blue nevus such as malignant blue nevus, cellular blue nevus, common blue nevus, nevus of Ito, or nevus of Ota; by detecting the presence of a mutation in a GNA11 gene or product encoded by the gene; or by detecting overexpression of GNA11. The methods can be used for diagnostic and prognostic indications and for identifying melanoma patients that are responsive, or likely to be responsive, to various treatment therapies that target the GNA11 pathway, such as G-alpha antagonists, or therapies that target downstream signaling components, such as protein kinase C inhibitors. The invention also provides methods of treating a melanoma or nevus comprising administering a GNA11 inhibitor, e.g., a small molecule, an antibody, or a nucleic acid inhibitor such as a siRNA, to a patient having the melanoma, e.g., uveal melanoma or malignant blue nevus; or nevus, e.g., a blue nevus, arising from a mutation in a GNA11 gene.

Thus, the invention provides a method of detecting a melanocytic neoplasm in a biological sample, e.g., a skin or eye sample, comprising melanoma cells from a patient, e.g., a patient that has, or is suspected of having, melanoma, the method comprising detecting an activating mutation of GNA11 in melanoma or nevi cells present in the biological sample, wherein the presence of an activating mutation of GNA11 is indicative of the presence of a melanocytic neoplasm. In some embodiments, the melanocytic neoplasm is a uveal melanoma. In other embodiments, the GNA11 mutation is indicative of a nevus, such as a blue nevus, or a melanoma arising in blue nevus, also known as malignant blue nevus. In some embodiments, the detecting step comprises detecting the presence or absence of a GNA11 mutation in a nucleic acid, e.g., mRNA or genomic DNA. In typical embodiments, such detection steps comprise an amplification reaction that specifically amplifies GNA11, such as PCR or RT-PCR and detection of a mutation using a probe that hybridizes to a target GNA11 sequence or by sequencing the amplified GNA11. In other embodiments, the detecting step comprises detecting the mutation in a GNA11 protein, e.g., measuring the level of GNA11 activity and/or expression. In typical embodiments, such detecting step comprises the use of antibodies (immunocytochemistry) and/or electrophoretic protein separation (e.g., western blot). In some embodiments the GNA11 mutation is Gln209 to Leu (CAA to CTA or CAA to CTG), while in other embodiments, the GNA11 mutation is Gln209 to Pro (CAA to CCA).

Typically, the detecting step comprises detecting the presence or absence of an activating sequence mutation in a GNA11. This is often achieved, e.g., by analyzing a nucleic acid sample from the biological sample. The nucleic acid can be a DNA or RNA sample. The DNA sample can be obtained from reverse transcription of RNA, or can be genomic DNA. Often, the detection step for detecting the mutation comprises an amplification reaction. The presence or absence of the mutations can be identified, e.g., by sequence analysis of the amplified nucleic acid; or by methods that employ allele-specific oligonucleotide primers or probes.

In some embodiments, the methods of the invention may comprise an additional step of detecting an the presence or absence of an activating mutation in GNAQ, e.g., a mutation at the codon encoding Gln 209 of GNAQ in a nucleic acid from the biological sample. In some embodiments, the biological sample is from a patient that has uveal melanoma or a malignant blue nevus. In some embodiments, the patient has a melanocytic neoplasm where the melanocytic neoplasm is a blue nevus.

In some embodiments, the biological sample is from a patient that has, or is suspected of having a melanoma, e.g., uveal melanoma or malignant blue nevus, or metastasis. In other embodiments, the biological sample is from a patient that has, or is suspected of having, a nevus, e.g., a blue nevus such as common blue nevus, cellular blue nevus, nevus of Ito, or nevus of Ota. In some embodiments, the sample is from skin, eye, or from a metastatic site.

The invention also provides a method of monitoring progression of melanoma in a patient subjected to a therapy for treatment of the melanoma arising from a mutation in GNA11. The method comprises detecting a change in the number of cells having a mutation in GNA11 in a biological sample from a patient, where the change in the number of cells having a mutation is indicative of the patient's response to the therapy. In some embodiments, the melanoma is uveal melanoma. In some embodiments, the melanoma is a malignant blue nevus. In some embodiments, the sample is from a metastatic site.

In some embodiments, monitoring progression of melanoma in a patient where the melanoma arose from an activating mutation in a GNA11 gene is performed by detecting the mutation in a nucleic acid from the biological sample. In other embodiments, the progression of the melanoma arising from a mutation in GNA11 is detected in by evaluating a GNA11 protein present in the biological sample. In some embodiments of the invention, the biological sample is from eye or skin. In other embodiments, the biological sample is from a metastatic site, e.g., liver, lung, blood, lymph node, adrenal gland, or bone.

Typically, in monitoring melanoma progression in accordance with the invention, the presence of a reduced number of cells having a GNA11 mutation in the biological sample taken from a patient after treatment with an agent as compared to the number of cells having a GNA11 mutation in a biological sample taken from the patient before being exposure to the treatment agent is indicative of a positive therapeutic response to the treatment agent.

In all of the detection methods of the invention the biological sample can be from any source in the body that is suspected of containing primary or metastatic melanoma cells. Thus, the biological sample can be from skin, e.g., eye, e.g., uvea, conjunctiva, or mucosal membranes. In other embodiments, the sample can be from blood, serum, tissue from lymph nodes, or tissue from visceral organs such as adrenal gland, liver or lung; or bone tissue. In some embodiments, for example in monitoring progression of melanoma, the sample is from a readily accessible tissue such as blood.

In another aspect, the invention provides a method of determining whether a melanoma patient is a candidate for receiving a therapy that inhibits the activity of a Gα subunit, either directly or by inhibiting a protein that is activated by Gα. The method comprises determining whether the melanoma cells have an activating mutation in GNA11. In some embodiments, patients treated with such inhibitors do not have a melanoma or nevus that has an activating mutation in GNAQ. This determination is performed in accordance with the detection methods described herein. Accordingly, the detecting step can comprise detecting the mutation in mRNA, DNA, or protein. In some embodiments, the detecting step can comprise detecting the presence of a GNA11 mutation in a nucleic acid sample from the melanoma or nevus, whereas in other embodiments, the detecting step is from a protein sample from a melanocytic neoplasm. The nucleic acid sample can be RNA or DNA, e.g., genomic DNA or cDNA made from RNA from the melanocytic neoplasm sample. Often, the detecting step comprises an amplification reaction, such as PCR or RT-PCR.

In some embodiments, the melanoma is a uveal melanoma.

In another aspect, the invention provides a method of inhibiting growth and/or proliferation of nevus or melanoma cells arising from a somatic mutation in GNA11, the method comprising administering a GNA11 antagonist. The GNA11 antagonist can be e.g., a small molecule, such as edelfosine, a protine kinase C inhibitor, or the staurosporine analogue CPG41251; an antibody; a peptide; or a nucleic acid. In some embodiments, the inhibitor is siRNA. In some embodiments the siRNA targets both GNA11 and GNAQ nucleic acid sequences. Typically, the nevi or melanoma cells are from e.g., uveal melanoma or a blue nevus. In typical embodiments, the patient undergoing treatment does not have a melanoma or nevus that has a mutation in GNAQ.

The invention also provides a method of determining the risk of progression of a nevus to a melanoma, the method comprising detecting the presence or absence of a sequence mutation in a GNA11 gene in a biological sample from the nevus, wherein the presence of the mutation is indicative of increased risk of progression of the nevus to melanoma. In some embodiments, the sequence mutation is a codon encoding Gln 209 of GNA11. In some embodiments, the nevus is a blue nevus. In some embodiments, the mutation is detected by evaluating the protein that is encoded by the gene.

The invention also provides a method of determining the risk of metastasis of a melanoma, the method comprising detecting the presence or absence of a sequence mutation in a GNA11 gene in a biological sample from the patient where the biological sample comprises primary melanoma cells and wherein the presence of the mutation is indicative of increased risk of metastasis of the melanoma. In some embodiments the melanoma is uveal melanoma. In some embodiments, the sequence mutation is a codon encoding Gln 209 of GNA11.

In some embodiments, a GNA11 mutation, e.g., an activating mutation at codon 209, is detected in a melanocytic neoplasm such as acral melanoma, acral lentiginous melanoma, chronic sun-induced damaged (CSD) melanoma, non-chronic sun-induced damage (NCSD) melanoma, lentigo maligna melanoma, muscosal melanoma, nodular melanoma, superficial spreading melanoma, desmoplastic melanoma, conjunctival melanoma, recurrent cellular blue nevi, melanoma arising in a congenital nevus, malignant blue nevus, and metastasis. In some embodiments, the GNA11 mutation is detected in melanocytic neoplasms that are nevi. For example, a GNA11 mutation may be detected in a congenital nevus, congenital nevus with nodules, congenital nevus with desmoplastic reaction, giant congenital nevus with atypia, giant congenital nevus with nodules, congenital nevus without specific diagnosis, atypical blue nevus, atypical cellular blue nevus, blue nevus with neurocristic hamartoma, blue nevus without specific diagnosis and deep penetrating nevus without specific diagnosis.

DETAILED DESCRIPTION OF THE INVENTION

Introduction

Figure 1:
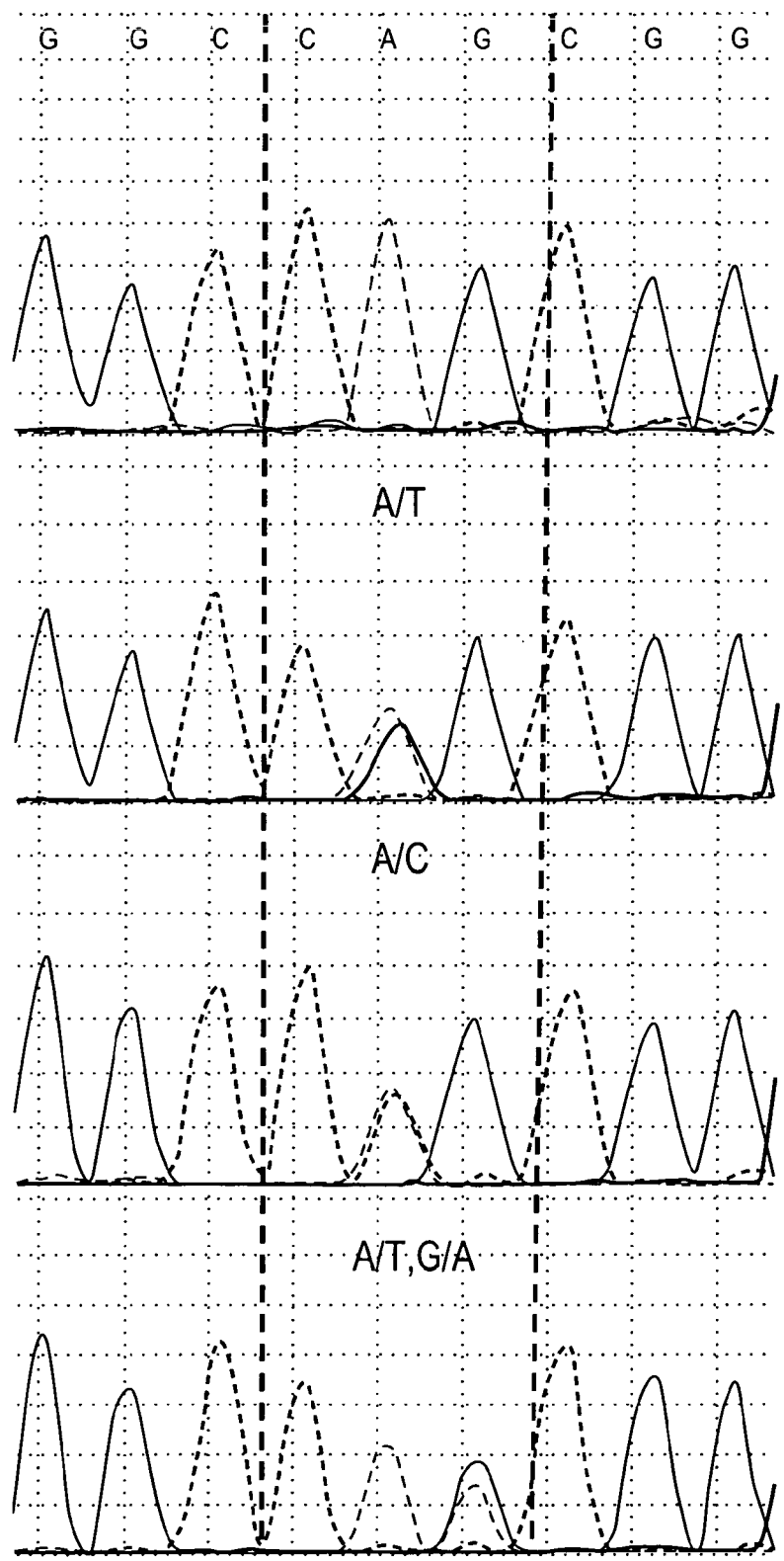
FIG. 1: Mutation spectrum of GNA11 at codon 209. The top panel shows the wild type sequence of codon 209 coding for glutamine (between dashed lines). The most common mutation was a adenine to thymine transversion resulting in a substitution to leucine (GNA11$^{Q209L}$), followed by a adenine to cytosine transversion resulting in a proline substitution (GNA11$^{Q209P}$) and a mutation affecting the second and third base of codon 209, also resulting in a leucine substitution.

The present invention provides methods, reagents and kits, for detecting melanoma and nevus cells for diagnostic and prognostic uses, and for treating melanomas and nevi. The invention is based, in part, upon the discovery that melanoma and nevi have activating somatic mutations in GNA11, i.e., mutations that result in a loss or decrease of GTP hydrolyzing activity of a G-α subunit.

G-α is the alpha subunit of one of the heterotrimeric GTP-binding proteins that form two subgroups in vertebrates, the widely expressed Gα-q family comprising Gnaq and Gna11, and the Gna14 and Gna15 family, which show more restricted expression. The Gα-q family mediates stimulation of phospholipase Cβ resulting in the hydrolysis of bisphosphoinositide (PIP$_2$) into inositide triphosphate (IP$_3$) and diacylglycerol (DAG). IP$_3$ can stimulate the release of calcium from intracellular storage in the endoplasmic reticulum (ER) leading to downstream calcium-dependent signaling. In parallel, DAG can activate protein kinase C (PKC) and both pathways can then feed into the mitogen activated protein kinase (MAPK) cascade. See, Corbit, K. C., et al., (2000) *Mol. Cell Biol.* 20:5392-5403; Sato, M. et al., (2006) *Ann. Rev. Pharm. Toxicol.* 46:151-187.

In one aspect of the invention, the present inventors have discovered that activating mutations in GNA11, e.g., heterozygous, somatic substitution mutations of Q209 of GNA11, are present in several types of melanocytic neoplasms, including nevi such as blue nevi and melanoma, such as uveal melanoma.

In some embodiments, a GNA11 activating mutation is a mutation that leads to overexpression of GNA11 nucleic acid and polypeptide sequences. Thus, in addition to methods of detecting activating mutations, methods that detect levels of GNA11 nucleic acid and/or polypeptide sequences can also be used to detect nevi, e.g., blue nevi and melanoma cells, such as primary or metastatic uveal melanoma cells, as described herein in which GNA11 is overexpressed.

In one aspect of the invention, the ability to detect nevi and/or melanoma cells by virtue of detecting a somatic mutation in GNA11 that activates GNA11, is useful for any of a large number of applications. For example, it can be used, alone or in combination with other diagnostic methods, to diagnose melanoma, or a certain type of melanoma, in the patient. It can also be used to identify particular melanomas that are sensitive to therapeutics, such as therapeutics that target G-proteins or phospholipase Cβ or other downstream components of pathways regulated by GNA11. In some embodiments, detection of an activating GNA11 mutations can be employed as a prognostic indicator of more aggressive melanomas that are more likely to lead to metastasis than melanomas that do not have a mutation in GNA11.

The detection of somatic activating mutations in GNA11 can also be used to monitor the efficacy of a melanoma treatment. For example, the level of GNA11 activity, e.g., Gα activity, or an activity such as phospholipase Cβ that is dependent on Gα activity, or the numbers of melanocytic cells that have a sequence mutation in GNA11, after an anti-melanoma treatment can be compared to the level before the treatment. A decrease in the level of GNA11 activity, e.g., phospholiapse Cβ activity, or a reduction in the number of melanoma cells that have mutated GNA11 after the treatment, indicates efficacious treatment.

The level of GNA11 activity and/or a change in the number of cells having a somatic mutation in GNA11 can also be statistically correlated with the efficacy of particular anti-melanoma therapy or with an observed prognostic outcome, thereby allowing the development of a database on which statistically-based prognosis, or a selection of the most efficacious treatment, can be made in view of a particular level activity or diagnostic presence of a GNA11 mutation.

Detection of cells having an activating mutation in GNA11 can be useful to monitor the number or location of melanoma cells in a patient, for example, to monitor the progression of the cancer over time.

The presence of an activating mutation in GNA11 can also indicate melanomas that are likely to be responsive to therapeutic agents that target mutant GNA11. Accordingly, the invention also provides methods of treating a melanocytic neoplasm, e.g., uveal melanoma or a blue nevus, that has an activating mutation in GNA11 by administering a Gα antagonist, e.g., antibodies, peptides, small molecule inhibitors, such as L-threo-dihydrosphingosine (a PKC specific inhibitor) or other small molecule inhibitors, and nucleic acid inhibitors of GNA11, e.g., GNA11 or GNA11/GNAQ siRNA inhibitors, or inhibitors of phospholipase Cβ, or downstream pathways regulated by GNA11. Such melanocytic neoplasms can be identified by analyzing for the presence of an activating mutation in GNA11 using the methods described herein.

The presence of an activating mutation in GNA11 in nevi often indicates nevi, e.g., conventional types of blue nevi and nevi of Ota, that are at risk for progression to melanoma. Accordingly, a nevus from a patient can be evaluated for the presence of an activating mutation using the methods described herein.

Definitions

The term "GNA11" or "Gna11" refers to the alpha subunit of a guanine nucleotide binding protein (G-protein). The term encompasses nucleic acid and polypeptide polymorphic variants, alleles, mutants, and fragments of GNA11. Human GNA11 is localized to chromosome region 19p13.3. GNA11 sequences are well known in the art. An example of a nucleic acid sequence encoding GNA11 is provided as SEQ ID NO:1. An example of a polypeptide sequence is shown in SEQ ID NO:2. A human GNA11 gene variant is localized to chromosome region 19p13.3 and encodes a polypeptide that has at least 97%, 98%, or 99%, or greater, identity to SEQ ID NO:2.

A "GNA11-dependent melanoma" as used in the context of this application refers to a melanocytic neoplasm comprising melanoma cells that have a defect (also referred to as a "mutation") in GNA11 that activates GNA11, i.e., has an "activating" mutation, in comparison to melanocytes that do not have the mutation, and leads to a loss or decrease of GTP hydrolyzing activity of the mutant G-α subunit. The defect in GNA11 can involve a mutation, e.g., a substitution mutation, that results in constitutive activity of the protein. The "GNA11-dependent melanoma cells" may have one or more of such mutations, e.g, the cells may have somatic substitution mutation involving Q209. A "GNA11-dependent melanoma" of the present invention can arise, e.g., from a nevus (e.g., a blue nevus) or the eye (e.g., the uvea). A "GNA11-dependent melanoma" may also have mutations in genes other than GNA11.

The term "mucosal melanoma" refers to tumors arising on mucosal membranes; "ocular melanoma" as used herein is melanoma that arises from the eye. "Ocular melanoma" includes uveal and conjunctival melanoma. "Conjunctival melanoma" refers to a melanoma that arises on the conjunctiva, while "uveal melanoma" refers to a melanoma of the pigmented tract of the eye.

"CSD melanoma" as used herein refers to melanoma arising from skin with chronic sun-induced damage; and "NCSD melanoma" as used herein refers to melanoma arising from skin without chronic sun-induced damage. The distinction between the "CSD" and "NCSD" groups in the instant application is based on a microscopic determination of the presence or absence of marked solar elastosis of the dermis surrounding the melanomas. In all but a few cases, melanomas associated with chronic sun-induced damage (CSD) occur on the face and distal extremities such as the forearms, dorsal hands, shins and calfs. These melanomas typically occur in individuals older than 50 years of age, and microscopically, have an intraepidermal component in which melanocytes are arranged as solitary units rather than nests. In addition, these melanomas tend to have an atrophic epidermis with the effacement of the rete ridges. A subset of the CSD melanomas is lentigo maligna melanomas. By contrast melanomas that were not associated with chronic sun-induced damage (NCSD) occur on the trunk and proximal extremities such as thighs and upper arms. The NCSD melanomas typically show an intraepidermal component in which melanocytes are arranged as nests rather than solitary units and display considerable upward scatter (pagetoid spread). Many of the NCSD melanomas are superficial spreading melanomas.

Chronic sun-induced damage is defined as having a CSD score greater than CSD 2. The scores are obtained by determining the degree of solar elastosis on hematoxylin-and-eosin (H&E) stained sections of normal skin surrounding the melanomas at 100-200× magnification using the following system (Landi et al., *Science* 313: 521-522, 2006), examples of which are provide in Landi.

CSD 0: absence of elastotic fibers; CSD 0+: rare elastotic fibers discernible only at 200× magnification;

CSD 1: scattered elastotic fibers lying as individual units, not as bushels, between collagen bundles; "−" or "+" classifiers were used to indicate whether the elastotic fibers were scarcely or densely scattered.

CSD 2: densely scattered elastotic fibers distributed predominantly as bushels rather than individual units; The "−" classifier was used to indicate that bushels were present, but elastotic fibers distributed as individual units predominated; The "+" classifier was used when larger aggregates of bushels formed, but preserving the outline of individual bushels instead of forming amorphous deposits;

CSD 3: amorphous deposits of blue-gray material with lost fiber texture; "−" only focal formation of amorphous deposits; "+" very large agglomerates of diffuse basophilic material.

As used herein, the term "determining that the melanoma arose from" a site, e.g., uvea, mucosa, conjunctiva, acral skin, skin having chronic sun-induced damage, or skin that does not have chronic sun-induced damage, refers to identifying the site of origin of a melanoma. Such a determination can be performed by visual inspection of a patient or by a pathology evaluation of the melanoma.

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms. The term "neoplastic" refers to both benign and malignant atypical growth.

The term "melanocytic neoplasm" as used herein refers to an area of hyperpigmentation relative to the surrounding tissue. Melanocytic neoplasms include both nevi and primary melanoma as well as melanoma that has metastasized to anywhere in the body. Thus, "melanocytic neoplasm" as used here include benign neoplasms. Similarly, the term "melanocyte" refers to both neoplastic and normal melanocytes. Typically, melanocytic neoplasms occur on skin, mucosal membranes, and the eye. Non-limiting melanocytic neoplasms include melanoma, e.g., acral lentiginous melanoma, CSD melanoma, NCSD melanoma, lentigo maligna melanoma, muscosal melanoma, nodular melanoma, superficial spreading melanoma, desmoplastic melanoma, uveal melanoma, conjunctival melanoma, recurrent cellular blue nevi, melanoma arising in a congenital nevus, malignant blue nevus, and metastasis. Melanocytic neoplasms as used herein also include nevi. For example, non-limiting examples of melanocytic neoplasms also include congenital nevus, congenital nevus with nodules, congenital nevus with desmoplastic reaction, giant congenital nevus with atypia, giant congenital nevus with nodules, congenital nevus without specific diagnosis, blue nevus, atypical blue nevus, atypical cellular blue nevus, blue nevus with neurocristic hamartoma, blue nevus without specific diagnosis and deep penetrating nevus without specific diagnosis.

The term "blue nevus" or "blue nevi" as used herein refers to an intradermal, i.e., within the dermal layer of the skin, melanocytic proliferation that exhibits increased pigmentation such that the nevus typically has a bluish color. A blue nevus, which can be congenital or acquired, may present in diverse ways ranging from discrete bluish moles (blue nevi) to large blue-gray patches affecting the conjunctiva and periorbital skin (nevus of Ota), shoulders (nevus of Ito), and the lower back (Mongolian spot). In some embodiments a "blue nevus" may be a "malignant blue nevus", i.e., a melanoma that arose within a blue nevus or of which certain portions resemble a blue nevus histopathologically.

"Biological sample" as used herein refers to a sample obtained from a patient suspected of having, or having a melanoma. In some embodiments, the sample may be a tissue biopsy, which refers to any type of biopsy, such as needle biopsy, fine needle biopsy, surgical biopsy, etc. The sample typically comprises a tissue sample, e.g., a skin tissue sample or eye sample, that harbors the melanocytic neoplasm, although the biological sample may also be derived from another, site, e.g., a site to which a melanoma may metastasize, or from the blood. In some cases, the biological sample may also be from a region adjacent to the melanocytic neoplasm.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984); Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the KIT nucleic acids, proteins and antibodies at any position. Any method known in the art for conjugating the antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. Similarly, a "recombinant protein" is a protein made using recombinant techniques, i.e., through the expression of a recombinant nucleic acid as depicted above.

The phrase "selectively (or specifically) hybridizes to" refers to the binding, duplexing, or hybridizing of a molecule to a particular nucleotide sequence under stringent hybridization conditions when that sequence is present in a mixture (e.g., total cellular or library DNA or RNA, an amplification reaction), such that the binding of the molecule to the particular nucleotide sequence is determinative of the presence of the nucleotide sequence is the mixture.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. An example of stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Illustrative "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The phrase "functional effects" in the context of assays for testing compounds that inhibit activity of a GNA11 protein includes the determination of a parameter that is indirectly or directly under the influence of the GNA11 protein or nucleic acid, e.g., a functional, physical, or chemical effect, such as the ability to decrease tumorigenesis, or alter GTP hydrolase activity. Activities or functional effect of GNA11 can include protein-protein interaction activity, e.g., the ability of GNA11 to bind an antibody or other protein with which it interacts; GTP hydrolase activity, the ability of GNA11 to bind GTP and/or GDP; contact inhibition and density limitation of growth; cellular proliferation; cellular transformation; changes in pigmentation; growth factor or serum dependence; tumor specific marker levels; invasiveness into Matrigel; tumor growth and metastasis in vivo, including measurement of tumor growth and tumor "take" in a model system; mRNA and protein expression in cells, including those undergoing metastasis, and other characteristics of cancer cells. "Functional effects" include in vitro, in vivo, and ex vivo activities.

As used herein, "inhibitors" or "antagonists" of GNA11 (e.g. "GNA11 antagonists") refer to modulatory molecules or compounds that, e.g., bind to, partially or totally block activity, decrease, prevent, delay activation, inactivate, desensitize, or down regulate the activity or expression of GNA11 protein, phospholipase Cβ, or downstream molecules regulated by GNA11, e.g., protein kinase C (PKC). Inhibitors can include siRNA or antisense RNA, genetically modified versions of GNA11 protein, e.g., versions with altered activity, as well as naturally occurring and synthetic GNA11 antagonists, antibodies, small chemical molecules and the like. GNA11 inhibitors for use in the invention are known in the art. For example, non-limiting examples of inhibitors suitable for use with the present invention can include inhibitors of PKC, for example, the relatively nonspecific PKC inhibitor staurosporine, the staurosporine analogue CPG41251, bryostatin-1, KAI-9803, 7-hydroxystaurosporine, L-threo-dihydrosphingosine (safingol), AHT956 and AEB071, the non-selective PKC inhibitor (PKC412), ilmofosine (BM 41 440), indolcarbazole Gö6796 which is a more specific inhibitor of the classical PKC isoforms including PKCμ, the PKC-alpha antisense inhibitor LY900003, and the PKC-beta inhibitors LY333531, LY317615 (Enzastaurin). An example of an antisense molecule suitable for use in depleting PKC-alpha mRNA is 5'-GTTCTCGCTGGTGAGTTTCA-3' (SEQ ID NO:3). Non-limiting illustrative inhibitors of phospholipase Cβ can include edelfosine and fluvirusin B[2]. Assays for identifying other inhibitors can be performed in vitro or in vivo, e.g., in cells, or cell membranes, by applying test inhibitor compounds, and then determining the functional effects on activity.

In some embodiments, samples or assays comprising GNA11 proteins that are treated with a potential inhibitor are compared to control samples without the inhibitor, to examine the effect on activity. Typically, control samples, e.g., melanoma cells, that have a GNA11 mutation and that are untreated with inhibitors are assigned a relative protein activity value of 100%. Inhibition of GNA11 is achieved when the activity value relative to the control is changed at least 20%, preferably 50%, more preferably 75-100%, or more. In some embodiments, an inhibitor will activate a particular activity, such as GTP hydrolysis, however, the net effect will be a decrease in the activity of GNA11q, e.g., in comparison to controls that have activated GNA11.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 (3$^{rd}$ ed. 1994).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four framework" regions interrupted by three hypervariable regions, also called complementarity-determining regions (CDRs).

References to "V$_H$" or a "VH" refer to the variable region of an immunoglobulin heavy chain of an antibody, including the heavy chain of an Fv, scFv, or Fab. References to "V$_L$" or a "VL" refer to the variable region of an immunoglobulin light chain, including the light chain of an Fv, scFv, dsFv or Fab.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, Nature 348:552-554; Hoogenboom & Winter, J. Mol. Biol. 227:381 (1991); and Marks et al., J. Mol. Biol. 222:581 (1991)), yeast cells (Boder and Wittrup, 1997, Nat Biotechnol 15:553-557), or ribosomes (Hanes and Pluckthun, 1997, Proc Natl Acad Sci USA 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584; 5,545,807; 5,545,806; 5,569,825; 5,625,126; 5,633,425; 5,661,016, and in the following scientific publications: (e.g., Jakobavits, Adv Drug Deliv Rev. 31:33-42 (1998), Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

General Recombinant Methods

This invention relies in part on routine techniques in the field of recombinant genetics, e.g., for methods used in detecting GNA11 or for the preparation of GNA11 polypeptides and nucleic acids. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-1999).

Identification of a GNA11 Sequence in a Sample From a Patient

In one aspect of the invention, the presence of an activating mutation in a GNA11 polynucleotide, e.g., mRNA or genomic DNA, or increased activity of a GNA11 protein and/or the presence of a sequence mutation in a GNA11 protein, is determined in biological samples suspected of comprising nevus, such as blue nevus, and/or melanoma, e.g., uveal melanoma or malignant blue nevus, cells.

In some embodiments activating mutations in GNA11 nucleic acids are determined. As noted, human GNA11 sequences are well known. Accordingly, the presence of mutations can be readily determined.

"Sequence mutation" as used in this application refers to changes in a polynucleotide sequence that result in changes to protein activity. Mutations can be nucleotide substitutions, such as single nucleotide substitutions, insertions, or deletions. GNA11 mutations in melanocytic neoplasms of the present invention are typically activating mutations that lead to constituitive activation of GNA11 activity. A GNA11 gene that is "mutated" in the context of this invention includes a GNA11 gene that is overexpressed such that the GNA11 pathway activity is upregulated and leads to abnormal growth of a nevus or melanoma cell.

An activating mutation detected in accordance with the invention is typically a sequence mutation. A mutation may be in any part of the GNA11 gene where the mutation leads to activation of GNA11. A common sequence mutation site is present at Q209. Mutations in GNA11 at Q209 include those shown in FIG. 1. As is understood in the art, the particular mutation is commonly referred to by the change in amino acid sequence that results from the mutation in the nucleic acid sequence.

In the present invention an altered level of GNA11 activity and/or a sequence mutation in GNA11 is detected for the diagnosis (or for prognostic indications) of melanocytic neoplasms, e.g., for the diagnosis of subtypes of melanoma such as uveal melanoma and nevi such as blue nevi. Thus, biological samples obtained from patients that have or are suspected of having a melanocytic neoplasm can be analyzed for mutations in the sequence of GNA11 mRNA or protein. The presence of a mutation is conveniently analyzed using samples of RNA, DNA, or protein.

In some embodiments, the methods of the invention may further comprise evaluating a biological sample from a patient for the presence or absence of an activating mutation in GNAQ, e.g., a mutation at the codon encoding Gln 209 of GNAQ in a nucleic acid from the biological sample. In some embodiments, the biological sample is from a patient that has uveal melanoma or a malignant blue nevus. In some embodiments, the patient has a melanocytic neoplasm where the melanocytic neoplasm is a blue nevus. Methods of detecting activating mutations in GNAQ are know (see WO 2008/098208).

Detection of Sequence Mutations in GNA11

In one embodiment, diagnostic and prognostic detection of a sequence mutation in GNA11 is performed by determining the presence of cells in a biological sample having a sequence mutation in GNA11. Methods of evaluating the sequence of a particular gene are well known to those of skill in the art, and include, inter alia, hybridization and amplification based assays. A sequence mutation in GNA11 in the instant invention can be determined using a probe that selectively hybridizes to the mutant sequence.

In some embodiments, the presence of a mutant GNA11 allele can be conveniently determined using DNA sequencing, such as pyrosequenceing, or other known sequencing techniques. Other detection methods include single-stranded conformational polymorphism or restriction fragment length polymorphism detection methods and denaturing gradient gel electrophoresis analysis.

In some embodiments, a GNA11 sequence mutation in a biological sample is determined by hybidzation of sample DNA or RNA to a probe that specifically hybridizes to a GNA11 sequence. The probes used in such applications specifically hybridize to the region of the GNA11 sequence harboring the mutation. Preferred probes are sufficiently long, e.g., from about 10, 15, or 20 nucleotides to about 50 or more nucleotides, so as to specifically hybridize with the target nucleic acid(s) under stringent conditions.

In some embodiments, a probe may be used to hybridize to the regions of GNA11 that encodes position 209 of GNA11. In some embodiments, a probe used to detect a mutations may selectively hybridize to a mutant codon 209 that has a mutations CAG>CTG, CAG>CCG, CAG>CTA, or CAG>CTT.

Any of a number hybridization-based assays can be used to detect a sequence mutation in GNA11 in the cells of a biological sample. For example, dot blots, array-based assays and the like can be used to determine GNA11 sequence mutations.

In some embodiments, amplification-based assays are used to detect sequence mutations in GNA11 or to measure the levels of GNA11 transcript. In such an assay, the target GNA11 nucleic acid sequence is specifically amplified in an amplification reaction (e.g., Polymerase Chain Reaction, or PCR). Examples of amplification-based assays can include RT-PCR methods well known to the skilled artisan (see, e.g., Ausubel et al., supra). Detailed protocols for PCR of DNA and RNA, including quantitative amplification methods, are known (see, e.g., Innis et al. (1990) PCR Protocols, A Guide to Methods and Applications, Academic Press, Inc. N.Y.; and Ausubel and Russell & Sambrook, both supra). The known nucleic acid sequences for GNA11 (see, e.g., SEQ ID NO:1) are sufficient to enable one of skill to routinely select primers to specifically amplify any portion of the gene so that GNA11 is targeted. Suitable primers for amplification of specific sequences can be designed using principles well known in the art (see, e.g., Dieffenfach & Dveksler, PCR Primer: A Laboratory Manual (1995)).

Other suitable amplification methods include, but are not limited to, ligase chain reaction (LCR) (see, Wu and Wallace (1989) *Genomics* 4: 560, Landegren et al. (1988) *Science* 241:1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

The presence of mutations in GNA11 DNA or RNA can also be determined using know techniques such as allele-specific oligonucleotide hybridization, which relies on distinguishing a mutant from a normal nucleic acid sequence using an oligonucleotide that specifically hybridizes to the mutant or normal nucleic acid sequence. This method typically employs short oligonucleotides, e.g., 15-20 nucleotides, in length, that are designed to differentially hybridize to the normal or mutant allele. Guidance for designing such probes is available in the art. The presence of a mutant allele is determined by measuring the amount of allele-specific oligonucleotide that hybridizes to the sample In other embodiments, the presence (or amount) of a normal or mutant GNA11 nucleic acid can be detected using allele-specific amplification or primer extension methods. These reactions typically involve use of primers that are designed to specifically target a normal or mutant allele via a mismatch at the 3' end of a primer. The presence of a mismatch effects the ability of a polymerase to extend a primer when the polymerase lacks error-correcting activity. The amount of amplified product can be determined using a probe or by directly measuring the amount of DNA present in the reaction.

Detection of levels of GNA11 nucleic acids, e.g., levels of normal and/or mutant GNA11 polynucleotides, or the presence of a GNA11 mutation can also be performed using a quantitative assay such as a 5'-nuclease activity (also referred to as a "TaqMan®" assay), e.g., as described in U.S. Pat. Nos. 5,210,015; 5,487,972; and 5,804,375; and Holland et al., 1988, Proc. Natl. Acad. Sci. USA 88:7276-7280. In such an assay, labeled detection probes that hybridize within the amplified region are added during the amplification reaction. In some embodiments, the hybridization probe can be an allele-specific probe that discriminates a normal or mutant allele. Alternatively, the method can be performed using an allele-specific primer and a labeled probe that binds to amplified product. In other embodiments, the probe may not discriminate between a mutant and normal allele.

As indicated above, in some embodiments, levels of GNA11 RNA are detected. Methods of detecting and/or quantifying the level of GNA11 gene transcripts (mRNA or cDNA made therefrom) using nucleic acid hybridization techniques are known to those of skill in the art. For example, expression levels of GNA11 can also be analyzed by techniques such as RT-PCR, e.g., using real-time RT-PCR using allele-specific primers or probes, dot blotting, in situ hybridization, RNase protection, probing DNA microchip arrays, and the like.

Overexpression of GNA11, either mutated sequences or normal nucleic acid and/or polypeptide sequences, can be detected, e.g., using quantitative sequences known in the art such as those described hereinabove. Overexpression is determined with reference to a control, e.g., a normal tissue or normal melanocytes.

Detection of GNA11 Polypeptide Sequences

Altered GNA11 expression and/or activity can also be detected by detecting GNA11 protein or activity. For example, detection of GNA11 protein activity or the presence of GNA11 proteins that have a mutation, can be used for diagnostic purposes or in screening assays. In some embodiments, the level of GNA11 or the presence of a normal or mutant GNA11 polypeptide in a sample is conveniently determined using immunological assays. In other embodiments, GNA11 activity can be used to determine the presence of activating mutation of GNA11 in a biological sample. The following section discusses immunological detection of GNA11 The section also relates to generation and engineering of antibodies that can be used, e.g., in therapeutic applications.

Immunological Detection GNA11

Antibodies can be used to detect GNA11 or can be assessed in the methods of the invention for the ability to inhibit GNA11. The detection and/or quantification of GNA11 can be accomplished using any of a number of well recognized immunological binding assays. A general overview of the applicable technology can be found in Harlow & Lane, Antibodies: A Laboratory Manual (1988) and Harlow & Lane, Using Antibodies (1999). Other resources include see also Methods in Cell Biology: Antibodies in Cell Biology, volume 37 (Asai, ed. 1993); Basic and Clinical Immunology (Stites & Terr, eds., 7th ed. 1991, and Current Protocols in Immunology (Coligan, et al. Eds, John C. Wiley, 1999-present). Immunological binding assays can use either polyclonal or monoclonal antibodies. In some embodiments, antibodies that specifically detect mutant GNA11 molecules may be employed.

Commonly used assays include noncompetitive assays (e.g., sandwich assays) and competitive assays. In competitive assays, the amount of GNA11 present in the sample is measured indirectly by measuring the amount of a known, added (exogenous) GNA11 displaced (competed away) from an anti-GNA11 antibody by the unknown GNA11 present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers, which are then detected according to standard techniques (see Monroe et al., Amer. Clin. Prod. Rev. 5:34-41 (1986)).

Antibodies to GNA11 are commercially available. In some embodiments, mutations to GNA11 can be detected using antibodies that specifically bind a mutant form, thus immunoassays can also be used to detect mutant GNA11 proteins.

GNA11 or a fragment thereof, e.g., the portion of the peptide frequently containing a sequence mutation, may be used to produce antibodies specifically reactive with GNA11 using techniques known in the art (see, e.g., Coligan; Harlow & Lane, both supra). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Such antibodies can be used for diagnostic or prognostic applications, e.g., in the detection of melanomas or for other cancers that exhibit increased expression or activity of GNA11.

Typically, polyclonal antisera with a titer of $10^4$ or greater are selected and tested for cross reactivity against non-GNA11 proteins or even other related proteins from other organisms, using a competitive binding immunoassay. Specific polyclonal antisera and monoclonal antibodies will usually bind with a Kd of at least about 0.1 mM, more usually at least about 1 µM, optionally at least about 0.1 µM or better, and optionally 0.01 µM or better.

In some embodiments, a GNA11 antibody may be used for therapeutic applications. For example, in some embodiments, such an antibody may used to reduce or eliminate a biological function of GNA11 as is described below. That is, the addition of anti-GNA11 antibodies (either polyclonal or preferably monoclonal) to a melanocytic neoplasm (or a cell population containing cancererous cells) may reduce or eliminate the neoplasm. Generally, at least a 25% decrease in activity, growth, size or the like is preferred, with at least about 50% being particularly preferred and about a 95-100% decrease being especially preferred.

Often, the antibodies to the GNA11 proteins for therapeutic applications are humanized antibodies (e.g., Xenerex Biosciences, Mederex, Inc., Abgenix, Inc., Protein Design Labs, Inc.). Human antibodies can also be produced using various techniques known in the art, including phage display libraries (Hoogenboom & Winter, J. Mol. Biol. 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

Detection of Activity

As appreciated by one of skill in the art, GNA11 activity can be detected to evaluate expression levels or for identifying inhibitors of activity. The activity can be assessed using a variety of in vitro and in vivo assays, including GTP and GDP binding activity, GTP-hydrolase activity, or measurement of phospholipase Cβ. In some embodiments GNA11 activity can be evaluated using additional endpoints, such as those associated with transformation or pigmentation. Such assays are described in greater detail in the examples and section detailing methods of identifying additional GNA11 inhibitors. Typically GNA11 activity is determined by measuring the ability to bind a protein to which it interacts, e.g., an antibody, ligand, or other protein, such as signaling molecules.

Disease Diagnosis/Prognosis

GNA11 nucleic acid and polypeptide sequences can be used for diagnosis or prognosis of a melanocytic neoplasm, e.g., a blue nevus, uveal melanoma, or malignant blue nevus, in a patient. For example, as described above, the sequence, level, or activity of GNA11 in a melanocytic neoplasm sample from a patient can be determined, wherein an alteration, e.g., an increase in the level of expression or activity of GNA11 or an activating sequence mutation in GNA11, indicates the presence or the likelihood of a melanocytic neoplasm.

The methods of the present invention can be used to determine the optimal course of treatment in a patient with cancer. For example, the presence of an activating mutation in GNA11, e.g., an activating sequence mutation, can indicate that certain therapeutics, such as those that target GNA11, phospholipase Cβ, or downstream pathways regulated by GNA11 will be beneficial to those patients. In addition, a correlation can be readily established between the number of melanocytic neoplasm cells having the mutation in GNA11, and the relative efficacy of one or another anti-melanoma agent. Such analyses can be performed, e.g., retrospectively, i.e., by analyzing for an activating mutation in samples taken previously from patients that have subsequently undergone one or more types of anti-cancer therapy, e.g., therapies that target G-proteins or phospholipase Cβ, or other downstream pathways regulated by GNA11, and correlating the number of melanocytic neoplasm cells having the mutation with the known efficacy of the treatment.

Often, such methods will be used in conjunction with additional diagnostic methods, e.g., detection of other melanoma indicators, e.g., cell morphology, and the like. In other embodiments, a tissue sample known to contain melanoma cells, e.g., from a tumor, will be analyzed for GNA11 activating mutations to determine information about the cancer, e.g., the efficacy of certain treatments, such as therapeutics that target GNA11, or downstream pathways regulated by GNA11

In some embodiments, analysis of melanoma cells for the presence of GNA11 activating mutations can be used to determine the prognosis of a patient with melanoma, e.g., uveal melanoma or malignant blue nevus, or for determining progression of the disease. A "diagnostic presence" can be increased levels of GNA11 mRNA or protein and/or activity, and/or the presence of activating sequence mutations in GNA11.

Any biological sample suspected of containing melanoma cells can be evaluated to determine progression. For example, tissues from visceral organs, such as liver or lung, blood, lymph nodes, bone and the like can be analyzed for the presence of GNA11 sequence mutations and or increased levels of GNA11 activity.

Inhibitors or Modulators of GNA11

In another aspect, this invention includes methods of treating melanoma that overexpress and/or have a mutation in GNA11 where the method comprises administering an inhibitor or GNA11 antagonist. Inhibitors and GNA11 antagonists are known. For example, non-limiting inhibitors suitable for use with the present invention can include specific and nonspecific inhibitors of PKC and various PKC isoforms including PKCµ and PKCε. Non-limiting inhibitors suitable for use with the present invention also include staurosporine, the staurosporine analogue CPG41251, bryostatin-1, KAI-9803, 7-hydroxystaurosporine, L-threo-dihydrosphingosine (safingol), the non-selective PKC inhibitor (PKC412), ilmofosine (BM 41 440), Gö6976, which is an indolcarbazole that more specifically inhibits the classical isoforms of PKC, including PCKµ, the PKC-alpha antisense inhibitor LY900003, and the PKC-beta inhibitors LY333531, LY317615 (Enzastaurin). Non-limiting inhibitors of phospholipase Cβ can include edelfosine and fluvirusin B[2], which are also suitable for use in the present invention.

Other inhibitors include inhibitors such as antibodies, peptide, nucleic acids, e.g., siRNA, and the like. As used herein, a GNA11 inhibitor can be a molecule that modulates GNA11 nucleic acid expression and/or GNA11 protein activity, or in some embodiments, downstream pathways regulated by GNA11. In some embodiments, a GNA11 inhibitor is an inhibitory RNA molecule that targets GNA11 nucleic acid sequences. In some embodiments, an inhibitory RNA molecule that targets GNA11 nucleic acid sequences may also target GNAQ nucleic acid sequences.

Method of identifying suitable siRNA that target GNA11 are well known in the art.

The ability to inhibit GNA11 can be evaluated using appropriate assays, e.g., by assaying GNA11 activity, e.g., GTP binding or GTP hydrolase activity and comparing the amount of activity to controls that are not treated with the inhibitor.

In another embodiment, mRNA and/or protein expression levels can be measured to assess the effects of a test compound on GNA11 expression levels. A host cell expressing GNA11 is contacted with a test compound for a sufficient time to effect any interactions, and then the level of mRNA or protein is measured. The amount of time to effect such interactions may be empirically determined, such as by running a time course and measuring the level of expression as a function of time. The amount of expression may be measured by using any method known to those of skill in the art to be suitable.

The amount of expression is then compared to the amount of expression in the absence of the test compound. A substantially identical cell may be derived from the same cells from which the recombinant cell was prepared but which had not been modified by introduction of heterologous DNA. A difference in the amount of expression indicates that the test compound has in some manner altered GNA11 levels.

In some assays to identify GNA11 inhibitors, samples that are treated with a potential inhibitor are compared to control samples to determine the extent of modulation. Control samples without the mutation and untreated with candidate inhibitors are assigned a relative activity value of 100. Inhibition of GNA11 is achieved when the activity value relative to the control is about 80%, optionally 50%, optionally 25-0%.

GNA11 inhibitors can be any small chemical compound, or a biological entity, e.g., a macromolecule such as a protein, sugar, nucleic acid or lipid.

In some embodiments, GNA11 inhibitors are small molecules that have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a Log P over 5 (or M Log P over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

Inhibiton of Expression

As noted above, nucleic acid inhibitors may also be used to decrease expression of GNA11. Therefore, a nucleotide sequence that specifically interferes with expression of GNA11 at the transcriptional or translational level can be used to treat a melanoma or nevus. In some embodiments, such a nucleic acid inhibitor may also target GNA11 nucleotide sequences that are sufficiently identical to GNAQ nucleic acid sequences so as to interfere with expression of GNAQ. An inhibitory nucleic acid approach may utilize, for example, siRNA and/or antisense oligonucleotides to block transcription or translation of GNA11 mRNA, either by inducing degradation of the mRNA with a siRNA or by masking the mRNA with an antisense nucleic acid.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferably about preferably about 20-30 base nucleotides, preferably about 20-25 nucleotides in length, e.g., 20, 21, 22, 23, 24, 25, 26, 27, 28, 29, or 30 nucleotides in length.

"Silencing" or "downregulation" refers to a detectable decrease of transcription and/or translation of a target sequence, i.e., the sequence targeted by the siRNA, or a decrease in the amount or activity of the target sequence or protein in comparison to the normal level that is detected in the absence of the interfering RNA or other nucleic acid sequence. A detectable decrease can be as small as 5% or 10%, or as great as 80%, 90% or 100%. More typically, a detectable decrease ranges from 20%, 30%, 40%, 50%, 60%, or 70%.

A DNA molecule that transcribes dsRNA or siRNA (for instance, as a hairpin duplex) also provides RNAi. For example, dsRNA oligonucleotides that specifically hybridize to a GNA11 nucleic acid sequence such as SEQ ID NO:1 can be used in the methods of the present invention.

Antisense oligonucleotides that specifically hybridize to GNA11 nucleic acid sequences can also be used to silence the transcription and/or translation of GNA11, and thus treat melanoma, e.g., uveal melanoma, or a nevus such as a blue nevus. Methods of designing antisense nucleic acids (either DNA or RNA molecules) are well known in the art. Antisense nucleic acids may comprise naturally occurring nucleotides or modified nucleotides such as, e.g., phosphorothioate, methylphosphonate, and -anomeric sugar-phosphate, backbone-modified nucleotides.

The ability of an inhibitor to modulate the expression of GNA11 can be evaluated using known methods. Such methods generally involve conducting cell-based assays in which test compounds are contacted with one or more cells expressing GNA11 and then detecting a decrease in expression (either transcript or translation product).

Melanoma Treatment and Administration of Pharmaceutical Compositions

Inhibitors of GNA11 can be administered to a patient for the treatment of a melanocytic neoplasm having a sequence mutation in GNA11. As described in detail below, the inhibitors are administered in any suitable manner, optionally with pharmaceutically acceptable carriers. In some embodiments, inhibitors of PKC or phospholipase Cβ are administered. Protocols for the administration of inhibitors are known and can be further optimized for melanoma patients based on principles known in the pharmacological arts (see, e.g., Remington: *The Science and Practice of Pharmacy,* 21st Edition, Philadelphia, Pa. Lippincott Williams & Wilkins, 2005).

The inhibitors can be administered to a patient at therapeutically effective doses to prevent, treat, or control a melanocytic neoplasm. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular GNA11 inhibitor employed and the condition of the subject, as well as the body weight or surface area of the area to be treated. The size of the dose also will be determined by the existence, nature, and extent of any adverse effects that accompany the administration of a particular compound in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

siRNA can be delivered to the subject using any means known in the art, including by injection, inhalation, or oral ingestion of the siRNA. Another suitable delivery system for siRNA is a colloidal dispersion system such as, for example, macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., *Trends Biochem. Sci.,* 6:77, 1981). Liposomes can be targeted to specific cell types or tissues using any means known in the art.

Delivery of antisense polynucleotides specific for GNA11 can be achieved using any means known in the art including, e.g., direct injection, inhalation, or ingestion of the polynucleotides. In addition, antisense polynucleotides can be delivered using a recombinant expression vector (e.g., a viral vector based on an adenovirus, a herpes virus, a vaccinia virus, or a retrovirus) or a colloidal dispersion system (e.g., liposomes).

A treatment that targets GNA11 can be administered with other melanoma therapeutics, either concurrently or before or after treatment with another melanoma thereapeutic agent.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Kits for Use in Diagnostic and/or Prognostic Applications

The invention also provides kits for diagnostic or therapeutic applications. For diagnostic/prognostic applications, such kits may include any or all of the following: assay reagents, buffers, GNA11 probes, primers, antibodies, or the like. In some embodiments a kit that comprises GNA11 diagnostic reagents may further comprise GNAQ diagnostic reagents. Such a kit may, for example, comprise a primer set to specifically amplify GNA11 and a primer set to specifically amplify GNAQ. Further, a kit may comprise a probe that detects a mutation, such as a mutation at the codon encoding position 209 of GNA11 and/or GNAQ. In some embodiments, the kit may comprise a probe specific for GNA11 and a probe specific for GNAQ, as well as probes that discriminate between mutant and wildtype alleles. Optionally, the kit may further comprises amplification primers for GNA11 and GNAQ.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Examination of Melanoma and Nevus Samples for Presence of GNA11 Sequence Mutation To determine whether GNA11 plays a role in human melanocytic neoplasia, the coding regions of GNA11 were sequenced in uveal melanomas and blue nevi. The GNA11 coding region was also sequenced in normal surrounding tissue from selected biopsies.

Methodology

Tissues

Archival, paraffin-embedded biopsies were retrieved from the archives of the Department of Ophthalmology, and the Dermatopathology Section of the Departments of Dermatology and Pathology of the University of California, San Francisco, the Department of Pathology of the University of British Columbia, Canada, the Department of Pathology of the Memorial Sloan Kettering Cancer Center, and the University of Graz, Austria. For each sample, DNA was extracted from sections of 5-20 μm thickness from which tumor-bearing tissue had been manually microdissected.

Sequencing

Sample DNA was amplified using PCR. The reaction conditions were 0.25 mM each dNTPs, 0.4×BSA (New England Biolabs), 1 U Hotstar Taq (Qiagen), 1× Hotstar Taq buffer (Qiagen), and 0.5 mM each primer: 5'-cgctgtgtcctttcaggatg-3' (SEQ ID NO:4) and 5'-ccacctcgttgtccgact-3' (SEQ ID NO:5) to examine GNA11 Q209. PCR consisted of 35 cycles of 95° C. (30 seconds), 58° C. (1 minute), and 72° C. (1 minute) after initial denaturation of 94° C. for 15 minutes. PCR reactions were purified using columns and then used as templates for sequencing reactions using Big Dye (ABI). Sequencing was performed in both directions. Samples identified with mutations in both sequencing directions were replicated at least twice. For samples with mutations, DNA was sequenced from the adjacent normal tissue, to determine whether the mutations were somatically acquired.

Plasmids

A plasmid with the entire GNA11 coding region containing the Q209L variant was obtained from UMR cDNA Resource Center. The wild-type counterpart was generated by site-specific mutagenesis of codon 209. The coding regions of both constructs were epitope-tagged with an N-terminal Myc-tag and cloned into Wzl retroviral expression vectors. The GNAQ and GNA11 constructs used in Western blots were obtained from the Missouri S&T cDNA resource center. They are internally Glu-Glu tagged, with altered residues at position 171-176 from AYLPTQ (SEQ ID NO:6) (Gaq) or GYLPTQ (SEQ ID NO:7) (Ga1 1) to EYMPTE (SEQ ID NO:8), and were cloned into Wzl-retrovirus vectors. All constructs were sequenced for confirmation.

Transduction

Viral supernatants were generated using appropriate packaging cell lines and transfected with 10 µg plasmid and lipofectamine 2000. Media were changed 16 hr after transfection and the virus was harvested 40 to 56 hr later. Melan-a cells were transduced and positively selected with blasticidin.

Western Blot Analysis

Cells were washed twice with ice-cold PBS and lysed in 50 mM Tris-HCl pH 7.8, 1% NP-40, 10% glycerol, 150mM NaCl, 1% sodium deoxycholate, 1% sodium dodecyl sulphate, supplemented with protease inhibitor, phosphatase inhibitor and EDTA (Pierce Biotechnologies). The protein content of the lysates was determined by the BCA Protein Assay Reagent (Pierce Biotechnologies). 15 µg of protein were separated by SDS-PAGE and transferred to Immobilon-P membrane (Millipore). Primary antibodies were pERK (E-4, Santa Cruz Biotechnology) and β-actin (Sigma). Secondary antibodies were labeled with horseradish peroxidase.

Cell Culture

Melan-a cells were cultured in glutamine-containing RPMI media supplemented with 10% FCS and 200 nM TPA.

Tumorigenicity Evaluation

Melan-a cells were transduced with GNA11 expression constructs or a β-galactosidase control vector, and selected with 5 µg/ml blasticidin over two weeks. These cells were then cultured, trypsinized, washed in PBS, and re-suspended in DMEM at ten million cells per milliliter. Four month old female NOD/SCID/interleukin 2 receptor [IL2r] $\gamma^{null}$ mice were injected with one million cells subcutaneously in both flanks. Mice were palpated weekly for the development of tumors and tumor sizes were determined using calipers.

Results

We obtained sequencing data from exons 5 of GNA11 and GNAQ for 713 cases (Table 1). Mutations were identified in GNA11 exon 5, all at glutamine 209, which would result in a substitution to leucine in most (97.3%) of the cases (GNA11$^{Q209L}$) with 2.7% of the cases with a mutation resulting in a proline substitution (GNA11$^{Q209P}$). Mutations affecting codon 209 in GNA11 were CAG>CTG (94.5%), CAG>CCG (2.7%), CAG>CTA (1.4%), and CAG>CTT (1.4%). In all cases, those samples that had a GNA11 mutation did not have a GNAQ mutation. The mutation frequency of GNA11 increased progressively from blue nevi (7%), to primary uveal melanomas (32%), to uveal melanoma metastases (57%), a pattern inverse to the distribution of GNAQ mutations, which were most common in blue nevi and least common in metastases (p=<0.001). GNA11 mutations were restricted to neoplastic tissue and not found in DNA extracted from surrounding non-lesional tissue, indicating that the mutations are somatic.

Because the segmental melanocytoses, Nevus of Ito and the Nevus of Ota, are sparsely cellular, it is possible that mutations were missed in some samples.

Figure 2:
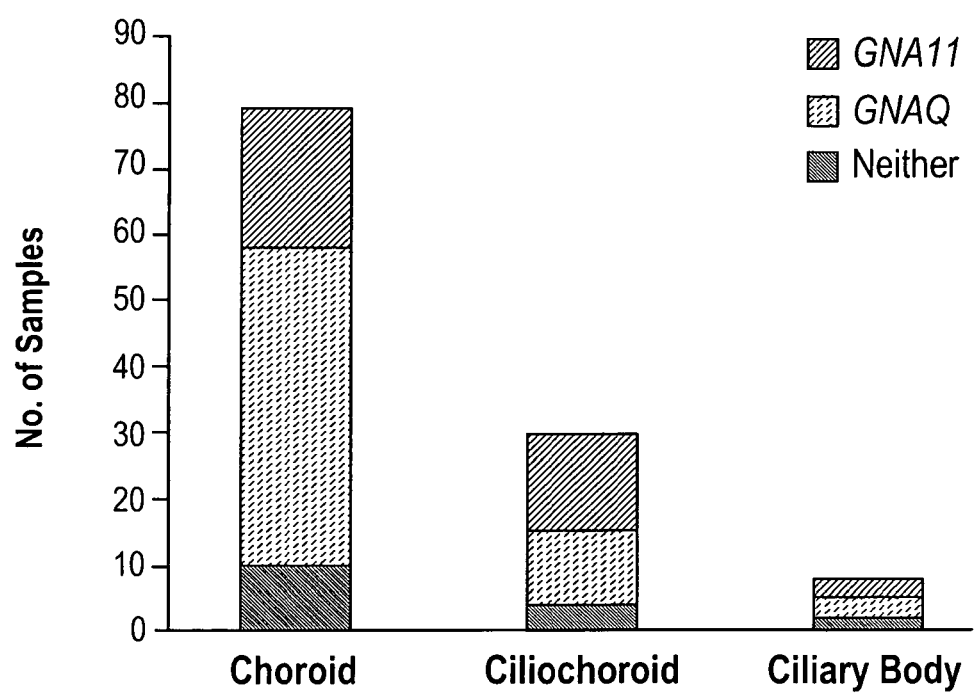
FIG. 2. Anatomic location and histopathological features and mutation status. A) GNA11 mutations were more common in primary uveal melanomas of ciliochoroidal location. (p=0.048, Fisher's Exact test). Bars: Upper segment, GNA11; middle segment, GNAQ; lower segment, neither
Figure 3:
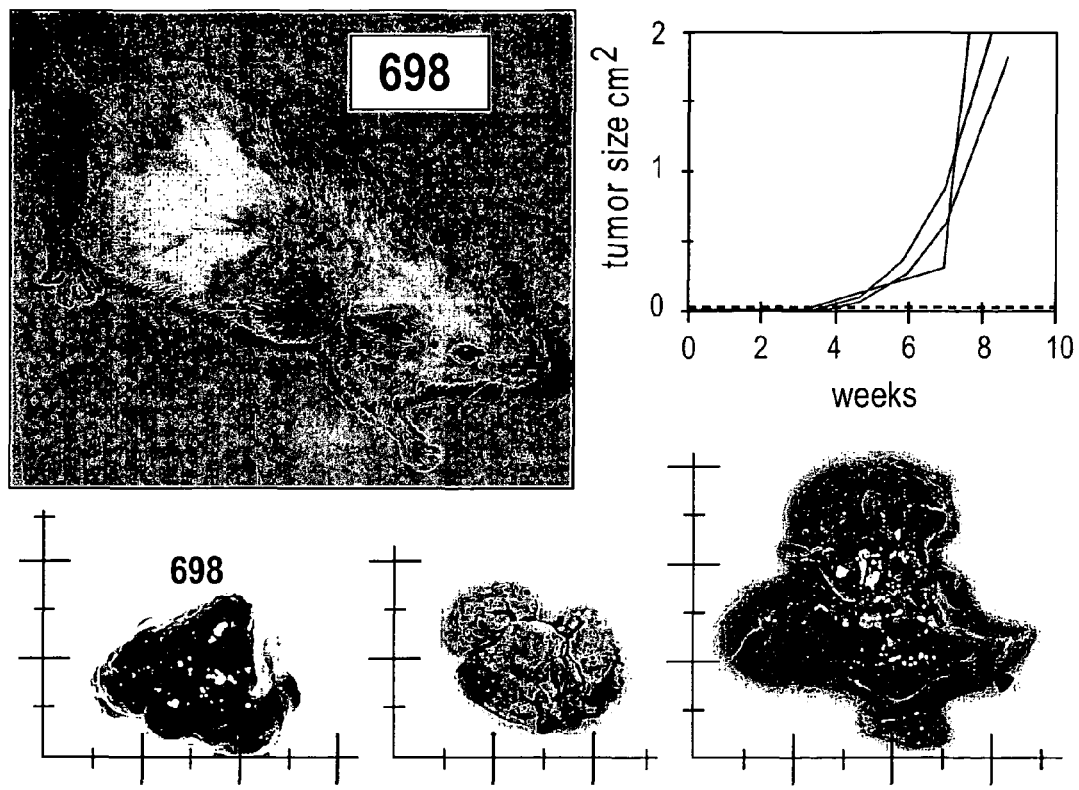
FIG. 3: GNA11$^{Q209L}$ induces tumors with spontaneous metastasis in immunocompromised mice. Immortalized mouse melanocytes (melan-a cells) were transduced with GNA11$^{Q209L}$ and injected bilaterally into the flank of NOD/SCID/interleukin 2 receptor [IL2r] $\gamma^{null}$ mice (n=5). All six injection sites developed tumors (upper right) that were heavily melanized (lower left), all mice developed multiple lung metastases (lower middle) and one mouse developed liver metastasis (lower right).
Figure 4:
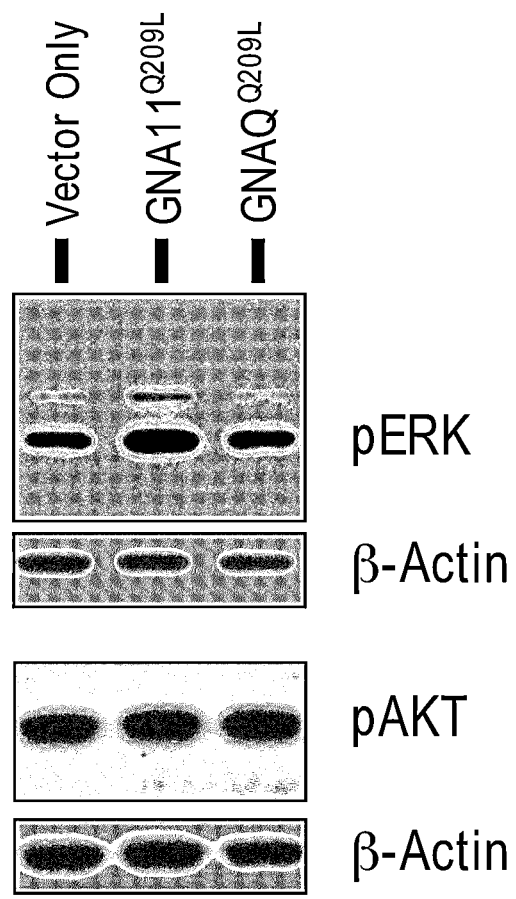
FIG. 4: Mutant GNA11 results in MAP-kinase activation. Melan-a cells were transduced with GNA11$^{Q209L}$, GNAQ$^{Q209L}$, or vector control, incubated for 48 hours, serum-starved for 16 hours, stimulated for 20 minutes with 2% serum, and lysed.

For the 118 cases of uveal melanoma in which it was possible to determine the location of the primary tumor, lesions arising in the ciliochoroidal regions had a higher frequency of GNA11 mutations (FIG. 2). Mutations of GNAQ and GNA11 were found more commonly in primary tumors with epithelioid cells or a mixture of epitheliod and spindled cells when compared to samples comprises of only spindled cells, but this was not statistically significant. Using Comparative Genomic Hybridization (CGH), we attempted to determine whether prognostically relevant chromosomal aberrations (e.g., White et al., Cancer 83:354-359, 1998) were present in 36 primary uveal melanomas and observed no association between their presence and mutation status of GNAQ and GNA11. However, this analysis was very limited, as none of the 35 samples was without a mutation for comparison.

Examination of overall survival and disease-free survival for the 81 cases for which we had the requisite data did not reveal a significant difference between those with tumors bearing a GNAQ mutation and those with tumors bearing a GNA11 mutations. A trend towards longer survival in those tumor carrying a GNA11 mutation, when compared with those tumors carrying a GNAQ mutation, or no GNAQ or GNA11 mutations, was observed, however.

Functional Validation of GNA11

To validate GNA11$^{Q209L}$ as an oncogene in vivo, immortalized mouse melanocytes (melan-a cells) were transduced with GNA11$^{Q209L}$ and monitored their ability to form tumors in immunocompromised mice compared with similar melanocytes transduced with β-galactosidase as negative controls). Each of six injection sites for GNA11$^{Q209L}$ melanocytes developed rapidly growing tumors. No tumors were observed at the injection sites of control melanocytes (n=6). In contrast to a comparable tumorigenicity experiment performed with GNAQ$^{Q209L}$-transduced melanocytes (Van Raamsdonk et al., Nature 457:599-602, 2009), all three mice injected with GNA11$^{Q209L}$ transduced melan-a cells developed metastases, three in the lung and one in the liver.

Western blot analyses of GNA11$^{Q209L}$-transduced melanocytes showed MAP-kinase activation, as measured by increased levels of phosphorylated ERK. In prior studies (e.g., Van Raamsdonk et al., Nature 457:599-602, 2009), GNAQ$^{Q209L}$ mutant cell lines were highly sensitive to MEK-inhibitors. Of the 13 uveal melanoma cell lines available in our laboratory, none carried a GNA11 mutation, and so we were unable to test whether the GNA11$^{Q209L}$ mutant cells are similarly sensitive to MEK-inhibitors. However, the close functional relationship between $G\alpha_q$ and $G\alpha_{11}$ together with the data that we describe here, indicates that the MAP-kinase activation is effected by GNA11$^{Q209}$ mutations in uveal melanoma cells and can be countered with MEK-inhibitors. Five of these thirteen cell lines carried the GNAQ$^{Q209}$ mutation, suggesting that GNA11 mutations compromise, to a greater extent than GNAQ$^{Q209}$ mutations, growth in culture.

Discussion

These data identified GNA11 as an oncogene frequently mutated in uveal melanoma. In our sample set, about 83% of uveal melanomas have a mutation in either GNAQ or GNA11, suggesting that activation of the $G\alpha_{q/11}$ pathway is the predominant route to the development of uveal melanoma. GNAQ and GNA11 share overlapping functions in melanocytes (Van Raamsdonk, et al., Nat Genet 36:961-8, 2004) and both activate the MAP kinase pathway when constitutively active. While Gαq and Gα11 have amino acid sequences that are 90% homologous, there appear to be differences in their role in melanocytic neoplasia.

GNA11 mutations may have a more potent effect on melanocytes than mutations in GNAQ. In the studies described in this example, GNA11 mutations were rare in blue nevi, which are benign neoplasms. There were significantly more GNA11$^{Q209}$ mutations than GNAQ$^{Q209}$ mutations in uveal melanoma metastases. Furthermore, GNA11 mutations were more common in locally advanced primary tumors and impriimaries originating from the cilliochoroidal regions, a prognostically adverse feature (Abramson et al., In Kufe et al., eds, Cancer Medicine, Neoplasms of the Eye, Adult Ophtalmic Oncology: Ocular Diseases: BC Decker, 2003). Finally, the mouse Gna11$^{Dsk7}$ mutation is more potent than Gnaq$^{Dsk1}$ at rescuing melanocyte proliferation/survival impaired by heterozygous mutations in Kit, Pax3 and endothelin B (Van Raamsdonk et al., *Nat Genet* 2004;36:961-968, 2004). However, as the mutations found in mice occur at different residues in GNA11 and GNAQ (I63V and V179M, respectively), it is possible that the difference is a functional consequence of the mutations, themselves, rather than a difference in function between GNA11 and GNAQ.

While patient survival did not differ significantly between GNAQ and GNA11-mutant cases in the study described in this example, the number of patients available at the time of the analysis may have been too small to detect such a difference. In addition, the analysis herein used enucleation specimens, which could have introduced a bias; tissue for mutation analysis is not routinely available from samples that do not undergo enucleation surgery. The samples that we analyzed in this example were also typically from larger tumors, which may have obscured association between GNAQ or GNA11 mutations and prognosis in the analysis in the present example.

In a recent study of GNAQ and GNA11 in 922 human neoplasms of various histopathologies, the only mutations found were in GNAQ in blue nevi (Lamba et al., *PLoS One* 4:e6833, 2009). Uveal melanoma was not included, however. While not exhaustive, these results and the data in the present study indicate that GNAQ and GNA11 mutations are enriched in the melanocytic lineage. Another study showed that GNAQ mutations were present in 37% of melanocytic neoplasms of the central nervous system (Kusters-Vandevelde, et al. *Acta Neuropathol* 2009. GNA11 mutations are also expected to be found in this category of melanocytic tumors.

Not to be bound by theory, the peculiar association of mutations in melanocytic neoplasms of the dermis, uvea and CNS may indicate different cells of origin. A developmental pathway has been described (Adameyko, et al., *Cell* 139:366-79, 2009) in which a subset of melanocytes derives from a precursor shared with Schwann cells. It is possible that Gα$_{q/11}$ signaling may have an important role in melanocytes arising through this developmental mechanism. If so, the timing when mutations arise may determine the localization and extent of the neoplasm. Lesions confined to the CNS would arise from Gαq/11 mutations in precursors before onset of migration, segmental lesions such as Nevus of Ota would result from mutations in a precursor early during migration, while mutations arising later along the migratory pathway would result in solitary lesions involving the skin or choroid.

In summary, the results presented in this example indicated that a large majority of uveal melanomas and blue nevi harbor mutations in either GNAQ or GNA11. The functional similarities between Gα$_q$ and Gα$_{11}$ thus form a basis to develop mechanism-based therapies for melanomas with these specific mutations. Such an intervention could benefit up to 83% of metastatic uveal melanoma cases, a particularly devastating form of melanoma for which no effective treatment is currently available.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Mutation frequency of Q209 in exons 5 of GNAQ and GNA11 in melanocytic neoplasms. CSD, melanoma located on chronically sun damaged skin; NonCSD, melanomas on skin without microscopic signs of chronic sun-induced damage.

| Categories | Subtypes | GNA11 | | GNAQ | | Neither | | Grand Total |
|---|---|---|---|---|---|---|---|---|
| Blue nevi | Amelanotic blue nevus | 0 | 0.0% | 7 | 70.0% | 3 | 30.0% | 10 |
| | Cellular blue nevus | 3 | 8.3% | 26 | 72.2% | 7 | 19.4% | 36 |
| | Common blue nevus | 4 | 6.7% | 39 | 65.0% | 17 | 28.3% | 60 |
| | Nevus of Ito | 0 | 0.0% | 0 | 0.0% | 7 | 100.0% | 7 |
| | Nevus of Ota | 1 | 5.0% | 2 | 10.0% | 17 | 85.0% | 20 |
| | Malignant blue nevus | 1 | 16.7% | 2 | 33.3% | 3 | 50.0% | 6 |
| | Total | 9 | 6.5% | 76 | 54.7% | 54 | 38.8% | 139 |
| Ocular melanocytic tumors | Conjunctival melanoma | 0 | 0.0% | 0 | 0.0% | 9 | 100.0% | 9 |
| | Uveal melanoma, primary | 52 | 31.9% | 73 | 44.8% | 38 | 23.3% | 163 |
| | Uveal melanoma, metastasis | 13 | 56.5% | 5 | 21.7% | 5 | 21.7% | 23 |
| | Uveal nevus | 0 | 0.0% | 1 | 100.0% | 0 | 0.0% | 1 |
| | Total | 65 | 33.2% | 79 | 40.3% | 52 | 26.5% | 196 |
| Other nevi | Common nevus | 0 | 0.0% | 0 | 0.0% | 22 | 100.0% | 22 |
| | Congenital nevus | 0 | 0.0% | 0 | 0.0% | 17 | 100.0% | 17 |
| | Deep penetrating nevus | 0 | 0.0% | 0 | 0.0% | 27 | 100.0% | 27 |

TABLE 1-continued

Mutation frequency of Q209 in exons 5 of GNAQ and GNA11 in melanocytic neoplasms. CSD, melanoma located on chronically sun damaged skin; NonCSD, melanomas on skin without microscopic signs of chronic sun-induced damage.

| Categories | Subtypes | GNA11 | | GNAQ | | Neither | | Grand Total |
|---|---|---|---|---|---|---|---|---|
| | Spitz nevus | 0 | 0.0% | 0 | 0.0% | 19 | 100.0% | 19 |
| | Atypical Spitz tumor | 0 | 0.0% | 0 | 0.0% | 20 | 100.0% | 20 |
| | Total | 0 | 0.0% | 0 | 0.0% | 105 | 100.0% | 105 |
| Extra-ocular melanomas | Acral | 0 | 0.0% | 0 | 0.0% | 47 | 100.0% | 47 |
| | CSD | 0 | 0.0% | 1 | 1.4% | 73 | 98.6% | 74 |
| | Mucosal | 0 | 0.0% | 0 | 0.0% | 62 | 100.0% | 62 |
| | NonCSD | 0 | 0.0% | 0 | 0.0% | 90 | 100.0% | 90 |
| | Total | 0 | 0.0% | 1 | 0.4% | 272 | 99.6% | 273 |
| | Grand Total | | | | | | | 713 |

Illustrative GNA11 cDNA and Protein Sequences:

SEQ ID NO: 1
Accession Number NM_002067 GNA11, mRNA, CDS243 . . . 1322

```
   1 gctgcggcgg cggcgcgggc tgagtgcggc cgcgcgggag tccgcggctg gcgcggcccg
  61 agcggggacc cggcggctcg ccaggcggcg gccgaggcgg ggcgggccgg cccggggccg
 121 agggccggtg gccgaggccg gagggccgcg gcgggcggcg gccgaggcgg ctccggccag
 181 ggccgggccg ggggccgggg ggcggcggcg ggcaggcggc cgcgtcggcc ggggccggga
 241 cgatgactct ggagtccatg atggcgtgtt gcctgagcga tgaggtgaag gagtccaagc
 301 ggatcaacgc cgagatcgag aagcagctgc ggcgggacaa gcgcgacgcc cggcgcgagc
 361 tcaagctgct gctgctcggc acgggcgaga gcgggaagag cacgttcatc aagcagatgc
 421 gcatcatcca cggcgccggc tactcggagg aggacaagcg cggcttcacc aagctcgtct
 481 accagaacat cttcaccgcc atgcaggcca tgatccgggc catggagacg ctcaagatcc
 541 tctacaagta cgagcagaac aaggccaatg cgctcctgat ccgggaggtg acgtggaga
 601 aggtgaccac cttcgagcat cagtacgtca gtgccatcaa gaccctgtgg gaggacccgg
 661 gcatccagga atgctacgac cgcaggcgcg agtaccagct ctccgactct gccaagtact
 721 acctgaccga cgttgaccgc atcgccacct tgggctacct gcccacccag caggacgtgc
 781 tgcgggtccg cgtgcccacc accggcatca tcgagtaccc tttcgacctg agaacatca
 841 tcttccggat ggtggatgtg ggggccagc ggtcggagcg gaggaagtgg atccactgct
 901 ttgagaacgt gacatccatc atgtttctcg tcgccctcag cgaatacgac caagtcctgg
 961 tggagtcgga caacgagaac cggatggagg agagcaaagc cctgttccgg accatcatca
1021 cctaccctg gttccagaac tcctccgtca tcctcttcct caacaagaag gacctgctgg
1081 aggacaagat cctgtactcg cacctggtgg actacttccc cgagttcgat ggtccccagc
1141 gggacgccca gcggcgcgg gagttcatcc tgaagatgtt cgtggacctg aaccccgaca
1201 gcgacaagat catctactca cacttcacgt gtgccaccga cacggagaac atccgcttcg
1261 tgttcgcggc cgtgaaggac accatcctgc agctcaacct caaggagtac aacctggtct
1321 gagcgcccag gcccagggag acgggatgga gacacggggc aggaccttcc ttccacggag
1381 cctgcggctg ccgggcgggt ggcgctgccg agtccgggcc ggggcctctg cccgcgggag
1441 gagatttttt tttttcatat ttttaacaaa tggtttttat ttcacagtta tcaggggatg
1501 tacatctctc cctccgtaca cttcgcgcac cttctcacct tttgtcaacg gcaaaggcag
1561 ccttttctg gccttgactt atggctcgct tttttctaaa aaaaaaaaaa aaaaa
```

-continued

SEQ ID NO: 2
GNA11 Protein Sequence
Accession Numbers: UniProtKB P29992-1; NP_002058

```
  1 MTLESMMACC LSDEVKESKR INAEIEKQLR RDKRDARREL KLLLLGTGES GKSTFIKQMR

61 IIHGAGYSEE DKRGFTKLVY QNIFTAMQAM IRAMETLKIL YKYEQNKANA LLIREVDVEK

121 VTTFEHQYVS AIKTLWEDPG IQECYDRRRE YQLSDSAKYY LTDVDRIATL GYLPTQQDVL

181 RVRVPTTGII EYPFDLENII FRMVDVGGQR SERRKWIHCF ENVTSIMFLV ALSEYDQVLV

241 ESDNENRMEE SKALFRTIIT YPWFQNSSVI LFLNKKDLLE DKILYSHLVD YFPEFDGPQR

301 DAQAAREFIL KMFVDLNPDS DKIIYSHFTC ATDTENIRFV FAAVKDTILQ LNLKEYNLV
```

---

What is claimed is:

1. A method of detecting an activating mutation in a GNA11 gene in a human melanoma patient that has a melanoma, wherein the melanoma is a uveal melanoma or a malignant blue nevus, the method comprising:
    contacting a nucleic acid sample from the melanoma with a probe that selectively hybridizes to a mutant GNA11 codon 209 that has a mutation CAG>CTG, CAG>CCG, CAG>CTA, or CAG>CTT; and
    detecting hybridization of the probe to the mutant GNA11 codon 209 that has a mutation CAG>CTG, CAG>CCG, CAG>CTA, or CAG>CTT.

2. The method of claim 1, wherein the sample is from eye or skin.

3. The method of claim 1, wherein the sample is from lymph node, lung, liver, adrenal gland, soft tissue, or bone.

4. The method of claim 1, wherein the melanoma is uveal melanoma.

5. The method of claim 1, wherein the melanoma is a malignant blue nevus.

* * * * *